(12) United States Patent
Klumpe et al.

(10) Patent No.: US 8,519,196 B2
(45) Date of Patent: Aug. 27, 2013

(54) C10 ALKANOLALKOXYLATE MIXTURES AND USE THEREOF AS NOVEL LOW-FOAMING WETTING AGENTS

(75) Inventors: Markus Klumpe, Mannheim (DE); Juergen Tropsch, Roemerberg (DE); Rolf-Dieter Kahl, Hassloch (DE); Roland Boehn, Fussgoenheim (DE); Susanne Stutz, Weinheim (DE); Ralf Noerenberg, Ingelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 915 days.

(21) Appl. No.: 10/575,760

(22) PCT Filed: Oct. 14, 2004

(86) PCT No.: PCT/EP2004/011575
§ 371 (c)(1),
(2), (4) Date: Apr. 13, 2006

(87) PCT Pub. No.: WO2005/037757
PCT Pub. Date: Apr. 28, 2005

(65) Prior Publication Data
US 2007/0065391 A1    Mar. 22, 2007

(30) Foreign Application Priority Data
Oct. 14, 2003  (DE) .................................. 103 48 420

(51) Int. Cl.
*C11D 3/20*  (2006.01)

(52) U.S. Cl.
USPC ........... 568/618; 568/620; 568/625; 510/505; 510/506; 510/421; 510/108

(58) Field of Classification Search
None
See application file for complete search history.

(56) References Cited

U.S. PATENT DOCUMENTS

| | | | | |
|---|---|---|---|---|
| 2,508,036 A | | 5/1950 | Kosmin | ......................... 568/622 |
| 4,969,953 A | * | 11/1990 | Miyazawa et al. | ............ 106/311 |
| 5,434,313 A | * | 7/1995 | Harrison et al. | .............. 568/461 |
| 7,173,138 B2 | * | 2/2007 | Ahlers et al. | ................... 548/101 |
| 7,371,716 B2 | * | 5/2008 | Ruland et al. | .................. 510/421 |
| 2005/0170991 A1 | * | 8/2005 | Ruland et al. | .................. 510/421 |

FOREIGN PATENT DOCUMENTS

| | | |
|---|---|---|
| DE | 102 18 753 | 11/2003 |
| DE | 102 43 363 | 4/2004 |
| EP | 0 667 893 | 8/1995 |
| WO | 94/11330 | 5/1994 |
| WO | 94/11331 | 5/1994 |
| WO | 00/74845 | 12/2000 |
| WO | 01/04183 | 1/2001 |
| WO | 03/091190 | 11/2003 |
| WO | WO 03091192 A1 * | 11/2003 |

OTHER PUBLICATIONS

Definition of amyl from TheFreeDictionary obtained from http://www.thefreedictionary.com/amyl on Feb. 16, 2010.*
U.S. Appl. No. 12/783,804, filed May 20, 2010, Seebeck, et al.
U.S. Appl. No. 12/783,726, filed May 20, 2010, Seebeck, et al.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

The alkoxylate mixtures comprise alkoxylates of the formula (I)

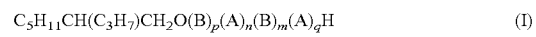

where
A is ethyleneoxy,
B, in each case independently, are $C_{3\text{-}10}$-alkyleneoxy or mixtures thereof,
groups A and B being present in the form of blocks in the stated sequence,
p is a number from 0 to 10,
n is a number greater than 0 to 20,
m is a number greater than 0 to 20,
q is a number greater than 0 to 10,
p+n+m+q is at least 1,
from 70 to 99% by weight of alkoxylates A1, in which $C_5H_{11}$ is n-$C_5H_{11}$, and
from 1 to 30% by weight of alkoxylates A2, in which $C_5H_{11}$ is $C_2H_5CH(CH_3)CH_2$ and/or $CH_3CH(CH_3)CH_2CH_2$, being present in the mixture.

8 Claims, No Drawings

C10 ALKANOLALKOXYLATE MIXTURES AND USE THEREOF AS NOVEL LOW-FOAMING WETTING AGENTS

The present invention relates to the use of $C_{10}$-alkanol alkoxylate mixtures, such $C_{10}$-alkanol alkoxylate mixtures and processes for their preparation.

Alkoxylates of aliphatic alcohols are used in large amounts as surfactants, emulsifiers and antifoams. The wetting and emulsifier properties depend to a great extent on the type of alcohol and on the type and amount of alkoxide adducts.

WO 94/11331 relates to the use of alkoxylates of 2-propylheptanol in detergent compositions for degreasing hard surfaces. The alkoxylates have from 2 to 16 alkylene oxide groups. Preferably, the predominant part of the alkylene oxide groups is present in the form of ethylene oxide. According to the examples, exclusively ethoxylated alcohols are used. It is furthermore stated that the alcohols can be reacted first with ethylene oxide and then with propylene oxide. However, no examples or properties are given for such alkoxylates. It is stated that the alkoxylates described exhibit a good detergent and wetting effect, in combination with little foaming. Moreover, it is stated that the alkoxylates have a desired thickening effect in formulations.

WO 94/11330 relates to alkoxylates of 2-propylheptanol and the use thereof. In the alkoxylates, 2-propylheptanol is present first as a reaction product with from 1 to 6 mol of propylene oxide and then as a reaction product with from 1 to 10 mol of ethylene oxide. According to the examples, a 2-propylheptanol reacted first with 4 mol of propylene oxide and then with 6 mol of ethylene oxide is used. It is stated that the alkylene oxide adducts exhibit an improved relationship of foam behavior to detergent effect. It is furthermore stated that the alkoxylates exhibit good wetting behavior. They are used in detergent compositions for cleaning textile materials.

U.S. Pat. No. 2,508,036 relates to the use of 2-n-propylheptanol ethoxylates which contain from 5 to 15 mol of ethylene oxide as wetting agents in aqueous solutions. It is stated that the products can be used as surfactants in detergents. Processes for the alkoxylation of 2-propylheptanol are known in principle from the prior art. WO 01/04183 describes, for example, a process for the ethoxylation of hydroxy-functional initiator compounds which is carried out in the presence of a double metal cyanide compound as a catalyst.

The non-prior-published DE-A-102 18 753 and DE-A-102 43 363 of earlier priority date relate to alkoxylate mixtures which are derived in particular from 2-propylheptanol by alkoxylation. There, either alkoxylation is effected exclusively with ethylene oxide or propylene oxide or alkoxylation is effected first with propylene oxide and then with ethylene oxide. It is stated that it is also possible for first ethylene oxide units and subsequently propylene oxide units to be present. In addition to random mixtures of ethylene oxide units and propylene oxide units, a 3-block or multiblock alkoxylation and mixed alkoxylations are also mentioned as possibilities.

It is an object of the present invention to provide alkanol alkoxylates which are suitable as an emulsifier, foam regulator and wetting agent for hard surfaces. The alkoxylates should in particular exhibit good emulsification behavior and a small contact angle on hard surfaces during use. Furthermore, they should reduce the surface tension in liquid systems. The alkoxylates should in general have an advantageous property spectrum when used as an emulsifier, foam regulator or wetting agent. Furthermore, it was intended to reduce the amount of residual alcohol in order to avoid odor annoyances.

We have found that this object is achieved, according to the invention, by alkoxylate mixtures comprising alkoxylates of the formula (I)

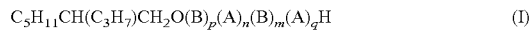

$$C_5H_{11}CH(C_3H_7)CH_2O(B)_p(A)_n(B)_m(A)_qH \qquad (I)$$

where
A is ethyleneoxy,
B, in each case independently, are $C_{3\text{-}10}$-alkyleneoxy, preferably propyleneoxy, butyleneoxy, pentyleneoxy or mixtures thereof,
groups A and B being present in the form of blocks in the stated sequence,
p is a number from 0 to 10,
n is a number greater than 0 to 20,
m is a number greater than 0 to 20,
q is a number greater than 0 to 10,
p+n+m+q is at least 1,
from 70 to 99% by weight of alkoxylates A1, in which $C_5H_{11}$ is n-$C_5H_{11}$, and
from 1 to 30% by weight of alkoxylates A2, in which $C_5H_{11}$ is $C_2H_5CH(CH_3)CH_2$ and/or $CH_3CH(CH_3)CH_2CH_2$,
being present in the mixture.

It has been found, according to the invention, that the above alkoxylate mixtures have excellent emulsifier properties and can be used as nonfoaming or slightly foaming wetting agents for hard surfaces. The alkoxylates have small contact angles in the wetting of hard surfaces and make it possible to establish low surface tensions in liquid systems.

The alkoxylate mixtures of the formula (I) can therefore particularly advantageously be used, in particular as an emulsifier, foam regulator and wetting agent for hard surfaces in surfactant formulations for cleaning hard surfaces, in humectants, cosmetic, pharmaceutical and crop protection formulations, finishes, coating materials, adhesives, leather degreasing agents, formulations for the textile industry, fiber processing, metal processing, food industry, water treatment, paper industry, fermentation or mineral processing, in emulsion polymerizations or for the preparation of additives or for application as additives for mineral building materials (for example, cement mortar, concrete, plaster, plaster screed, cement screed, etc.). The individual applications will be discussed in more detail below.

In the formula (I), p is a number from 0 to 10, preferably from 0 to 5, in particular from 0 to 3. If blocks $(B)_p$ are present, p is preferably a number from 0.1 to 10, particularly preferably from 0.5 to 5, in particular from 1 to 3.

In the formula (I), n is preferably a number in the range from 0.25 to 10, in particular from 0.5 to 7, m is preferably a number in the range from 2 to 10, in particular from 3 to 6. B is preferably propyleneoxy and/or butyleneoxy, especially propyleneoxy in both positions.

q is preferably a number in the range from 1 to 5, particularly preferably in the range from 2 to 3.

The sum p+n+m+q is at least 1, preferably from 3 to 25, particularly preferably from 5 to 15, in particular from 7 to 13.

In the novel alkoxylates, 3 or 4 alkylene oxide blocks are present. According to an embodiment, first ethyleneoxy units are adjacent to the alcohol radical, followed by propylene oxide units and thereafter ethyleneoxy units. According to a further embodiment, first propyleneoxy units are adjacent to the alcohol radical, followed by ethyleneoxy units, thereafter propyleneoxy units and finally ethyleneoxy units. Instead of the propyleneoxy units, the other stated alkyleneoxy units may also be present.

p, n, m and q are a mean value which is obtained as an average for the alkoxylates. p, n, m and q may therefore also differ from integral values. The alkoxylation of alkanols generally results in a distribution of the degree of alkoxylation, which can be established to a certain extent by using different alkoxylation catalysts. The property spectrum of the novel alkoxylate mixtures can be adapted to the practical requirements by the choice of suitable amounts of the groups A and B.

The novel alkoxylate mixtures are obtained by alkoxylation of the parent alcohols $C_5H_{11}CH(C_3H_7)CH_2OH$. The starting alcohols can be mixed from the individual components so that the novel ratio results. They can be prepared by aldol condensation of valeraldehyde and subsequent hydrogenation. The preparation of valeraldehyde and the corresponding isomers is effected by hydroformylation of butene, as described, for example, in U.S. Pat. No. 4,287,370; Beilstein E IV 1, 32 68, Ullmanns Encyclopedia of Industrial Chemistry, 5th Edition, Volume A1, pages 323 and 328 et seq. The subsequent aldol condensation is described, for example, in U.S. Pat. No. 5,434,313 and Römpp, Chemie Lexikon, 9th Edition, key word "Aldol Addition", page 91. The hydrogenation of the aldol condensate follows general hydrogenation conditions.

Furthermore, 2-propylheptanol can be prepared by condensation of 1-pentanol (as a mixture of the corresponding methylbutan-1-ols) in the presence of KOH at elevated temperatures, cf. for example Marcel Guerbet, C.R. Acad Sci Paris 128 (1899), 511, 1002. Furthermore, reference is made to Römpp, Chemie Lexikon, 9th Edition, Georg Thieme Verlag Stuttgart, and the citations mentioned there, and Tetrahedron, Vol. 23, pages 1723 to 1733.

In the formula (I), the radical $C_5H_{11}$ may be n-$C_5H_{11}$, $C_2H_5CH(CH_3)CH_2$ or $CH_3CH(CH_3)CH_2CH_2$. The alkoxylates are mixtures,
from 70 to 99, preferably from 85 to 96, % by weight of alkoxylates A1, in which $C_5H_{11}$ is n-$C_5H_{11}$, and
from 1 to 30, preferably from 4 to 15, % by weight of alkoxylates A2, in which $C_5H_{11}$ is $C_2H_5CH(CH_3)CH_2$ and/or $CH_3CH(CH_3)CH_2CH_2$, being present.

The radical $C_3H_7$ is preferably n-$C_3H_7$.

Preferably, the alkoxylation is catalyzed by strong bases, which are expediently added in the form of an alkali metal alcoholate, alkali metal hydroxide or alkaline earth metal hydroxide, as a rule in an amount of from 0.1 to 1% by weight, based on the amount of the alkanol $R^2$—OH (cf. G. Gee et al., J. Chem. Soc. (1961), 1345; B. Wojtech, Makromol. Chem. 66 (1966), 180).

An acidic catalysis of the addition reaction is also possible. In addition to Bronsted acids, Lewis acids are also suitable, for example $AlCl_3$ or $BF_3$ dietherate, $BF_3$, $BF_3 \cdot H_3PO_4$, $SbCl_4 \cdot 2H_2O$ or hydrotalcite (cf. P. H. Plesch, The Chemistry of Cationic Polymerization, Pergamon Press, New York (1963). Double metal cyanide (DMC) compounds are also suitable as a catalyst.

DMC compounds which may be used are in principle all suitable compounds known to a person skilled in the art.

DMC compounds suitable as a catalyst are described, for example, in WO 99/16775 and DE-A-101 17 273. Double metal cyanide compounds of the formula I:

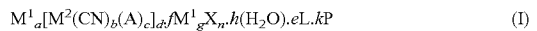

$$M^1{}_a[M^2(CN)_b(A)_c]_d \cdot fM^1{}_gX_n \cdot h(H_2O) \cdot eL \cdot kP \qquad (I)$$

where
$M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$ and $Ru^{3+}$, $M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, and $Ir^{3+}$, A and X, independently of one another, are an anion selected from the group consisting of halide, hydroxide, sulfate, carbonate, cyanide, thiocyanate, isocyanate, cyanate, carboxylate, oxalate, nitrate, nitrosyl, hydrogen sulfate, phosphate, dihydrogen phosphate, hydrogen phosphate and bicarbonate, L is a water-miscible ligand selected from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphites, phosphanes, phosphonates and phosphates, k is a fraction or integer greater than or equal to zero and P is an organic additive, a, b, c, d, g and n are selected so that the electroneutrality of the compound (I) is ensured, it being possible for c to be 0, e is the number of ligand molecules and is a fraction or integer greater than 0 or is 0, f and h, independently of one another, are a fraction or integer greater than 0 or are 0, are particularly suitable as a catalyst for the alkoxylation.

Examples of organic additives P are: polyether, polyester, polycarbonates, polyalkylene glycol sorbitan ester, polyalkylene glycol glycidyl ether, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylenimines, maleic acid and maleic anhydride copolymers, hydroxyethylcellulose, polyacetates, ionic surface-active and interface-active compounds, gallic acid or salts, esters or amides thereof, carboxylic esters of polyhydric alcohols and glycosides.

These catalysts may be crystalline or amorphous. Where k is zero, crystalline double metal cyanide compounds are preferred. Where k is greater than zero, crystalline, semicrystalline and substantially amorphous catalysts are preferred.

Among the modified catalysts, there are various preferred embodiments. One preferred embodiment comprises catalysts of the formula (I) in which k is greater than zero. The preferred catalyst then contains at least one double metal cyanide compound, at least one organic ligand and at least one organic additive P.

In another preferred embodiment, k is zero, e is also optionally zero and X is exclusively a carboxylate, preferably formate, acetate and propionate. Such catalysts are described in WO 99/16775. In this embodiment, crystalline double metal cyanide catalysts are preferred. Double metal cyanide catalysts as described in WO 00/74845, which are crystalline and lamellar, are furthermore preferred.

The preparation of the modified catalysts is effected by combining a metal salt solution with a cyanometallate solution which may optionally contain both an organic ligand L and an organic additive P. The organic ligand and optionally the organic additive are then added. In a preferred embodiment of the catalyst preparation, an inactive double metal cyanide phase is first prepared and this is then converted into an active double metal cyanide phase by recrystallization, as described in PCT/EP01/01893.

In another preferred embodiment of the catalysts, f, e and k are not equal to zero. These are double metal cyanide catalysts which contain a water-miscible organic ligand (generally in amounts of from 0.5 to 30% by weight) and an organic additive (generally in amounts of from 5 to 80% by weight), as described in WO 98/06312. The catalysts can be prepared either with vigorous stirring (24 000 rpm using a Turrax) or with stirring, as described in U.S. Pat. No. 5,158,922.

Double metal cyanide compounds which contain zinc, cobalt or iron or two thereof are particularly suitable as a catalyst for the alkoxylation. For example, Prussian Blue is particularly suitable.

Crystalline DMC compounds are preferably used. In a preferred embodiment, a crystalline DMC compound of the Zn—Co type, which contains zinc acetate as a further metal salt component, is used as a catalyst. Such compounds crystallize with a monoclinic structure and have a lamellar habit. Such compounds are described, for example, in WO 00/74845 or PCT/EP01/01893.

DMC compounds suitable as a catalyst can in principle be prepared by all methods known to a person skilled in the art. For example, the DMC compounds can be prepared by direct precipitation, the incipient wetness method, by preparation of a precursor phase and subsequent recrystallization.

The DMC compounds can be used in the form of a powder, paste or suspension or can be shaped to give a molding, introduced into moldings, foams or the like, or applied to moldings, foams or the like.

The catalyst concentration used for the alkoxylation is typically less than 2000 ppm (i.e. mg of catalyst per kg of product), preferably less than 1000 ppm, in particular less than 500 ppm, particularly preferably less than 100 ppm, for example less than 50 ppm or 35 ppm, particularly preferably less than 25 ppm, based on the final amounts.

The addition reaction is carried out at temperatures of from 90 to 240° C., preferably from 120 to 180° C., in a closed vessel. The alkylene oxide or the mixture of different alkylene oxides is added to the mixture of novel alkanol mixture and alkali under the vapor pressure of the alkylene oxide mixture prevailing at the chosen reaction temperature. If desired, the alkylene oxide may be diluted with up to about 30 to 60% of an inert gas. This provides additional safety by inhibiting explosive polyaddition of the alkylene oxide.

If an alkylene oxide mixture is used, polyether chains are formed in which the different alkylene oxide building blocks are virtually randomly distributed.

Variations in the distribution of the building blocks along the polyether chain are the result of different reaction rates of the components and may also be reached randomly by continuous feeding of an alkylene oxide mixture having a program-controlled composition. If the different alkylene oxides are reacted in succession, polyether chains having a block-like distribution of the alkylene oxide building blocks are obtained.

The length of the polyether chains varies within the reaction product randomly about a mean value, the stoichiometric value resulting substantially from the amount added.

Preferred alkoxylate mixtures of the formula (I) can be obtained according to the invention by reacting alcohols of the formula $C_5H_{11}CH(C_3H_7)CH_2OH$ with propylene oxide/ethylene oxide in the abovementioned sequence under alkoxylation conditions. Suitable alkoxylation conditions are described above and in Nikolaus Schönfeldt, Grenzflächenaktive Äthylenoxid-Addukte, Wissenschaftliche Verlagsgesellschaft mbH Stuttgart 1984. As a rule, the alkoxylation is carried out in the presence of basic catalysts, such as KOH, in the absence of a solvent. The alkoxylation can, however, also be carried out in the presence of a solvent. A polymerization of the alkylene oxide is initiated in which a random distribution of homologs whose mean value is stated here as p, n, m and q inevitably results.

In a propoxylation which, according to the invention, is preferably carried out first and is only then followed by an ethoxylation, the content of residual alcohol in the alkoxylates can be reduced since propylene oxide undergoes addition more uniformly at the alcohol component. In contrast, ethylene oxide preferably reacts with ethoxylates, so that a broader homolog distribution can result in the case of an initial use of ethylene oxide for reaction with the alkanols. The alcohol mixtures used according to the invention have, as a rule, a natural odor which can be very substantially suppressed by complete alkoxylation. Alkoxylates obtained by conventional processes often have a natural odor which is troublesome for many applications.

The novel alkoxylate mixtures require only one propylene oxide (PO) block of very short length, preferably directly bonded to the alcohol, for reducing the residual alcohol content. This is very advantageous in particular because the biodegradability of the product decreases with an increase in the length of the PO block. Such alkoxylate mixtures thus permit maximum degrees of freedom in the choice of the length of the PO block, the lower limit of the length being determined by the increasing residual alcohol content and the upper limit by the deterioration in the biodegradability.

It is not necessary according to the invention for a large residual content of alcohol to be present in the novel alkoxylate mixtures. According to an embodiment of the invention, the alkoxylate mixtures have a reduced content of alcohols or contain no alcohols.

The novel alkoxylate mixtures exhibit improved wetting on hard surfaces.

The advantageous wetting behavior of the novel mixtures can be determined, for example, by measurements of the contact angle on glass, polyethylene oxide or steel. The improved wetting behavior results in better performance particularly in rapid cleaning processes. This is surprising because the dynamic and wetting properties are usually reduced by the chain lengthening of the starting alcohol. The wetting speed of aqueous formulations can therefore be increased by means of the novel alkoxylate mixtures. The novel alkoxylate mixtures can thus also be used as solubilizers which have a positive instead of a negative influence particularly on the wetting capacity of wetting assistants also in dilute systems. They can be used for increasing the solubility of wetting assistants in aqueous formulations which contain nonionic surfactants. They serve in particular for increasing the wetting rate in aqueous wetting agents.

Furthermore, the novel alkoxylate mixtures serve for reducing the surface tension, for example in aqueous surfactant formulations. The reduced surface tension can be determined, for example, by the pendant drop method. This also indicates better effect of the novel alkoxylate mixtures as emulsifier or coemulsifier. The novel alkoxylate mixtures can also be used for reducing the surface tension for short times, usually less than one second, or for accelerating the establishment of the surface tension in aqueous surfactant formulations.

The present invention also relates to cleaning agents, wetting agents, coating materials, adhesives, leather degreasing agents, humectants or textile treatment compositions, starting materials for the preparation of additives for mineral building materials or additives for mineral building materials or cosmetic, pharmaceutical or crop protection formulations which contain at least one alkoxylate mixture as defined above and of the formula (I). The compositions preferably contain from 0.1 to 20% by weight of the alkoxylate mixtures. Preferred fields of use of the novel alkoxylate mixtures are described in more detail below. The novel alkoxylate mixtures are preferably used in the following areas:

Surfactant formulations for cleaning hard surfaces: suitable surfactant formulations to which the novel alkoxylates can be added are described, for example, in Formulating Detergents and Personal Care Products by Louis Ho Tan Tai, AOCS Press, 2000.

They contain, for example, as further components, soap, anionic surfactants, such as LAS or paraffinsulfonates or FAS or FAES, acid, such as phosphoric acid, amidosulfonic acid, citric acid, lactic acid or acetic acid, other organic and inorganic acids, solvents, such as ethylene glycol or isopropanol, complexing agents, such as EDTA, NTA, MGDA, or phosphonates, polymers, such as polyacrylates, maleic acid/acrylic acid copolymers, alkali donors, such as hydroxides, silicates, carbonates, perfume oils, oxidizing agents, such as perborates, per acids or trichloroisocyanuric acid, sodium or potassium dichloroisocyanurates, enzymes; cf. also Milton J. Rosen, Manilal Dahanayake, Industrial Utilization of Surfactants, AOCS Press, 2000, and Nikolaus Schönfeldt, Grenzflächenaktive Ethylenoxidaddukte. Here, formulations for the other applications mentioned are also discussed in principle. They may be household cleaners, such as general purpose cleaners, dishwashing agents for manual as well as automatic dishwashers, metal degreasing, industrial applications, such as cleaning agents for the food industry, bottle washing, etc. They may also be cleaning agents for impression rollers and printing plates in the printing industry. Suitable further ingredients are known to a person skilled in the art.

Humectants, in particular for the printing industry.

Cosmetic, pharmaceutical and crop protection formulations. Suitable crop protection formulations are described, for example, in EP-A-0 050228. Further ingredients customary for crop protection agents may be present.

Finishes, coating materials, paints, pigment preparations and adhesives in the surface coatings and film industry.

Leather degreasing agents.

Formulations for the textile industry, such as leveling agents or formulations for yarn cleaning.

Fiber processing and assistants for the paper and pulp industry.

Metal processing, such as metal finishing and electroplating.

Food industry.

Water treatment and provision of drinking water.

Fermentation.

Mineral processing and dust control.

Building assistants.

Emulsion polymerization and preparation of dispersions.

Coolants and lubricants.

Such formulations usually contain ingredients such as surfactants, builders, fragrances and dyes, complexing agents, polymers and other ingredients. Typical formulations are described, for example, in WO 01/32820. Further ingredients suitable for different applications are described by way of example in EP-A-0 620 270, WO 95/27034, EP-A-0 681 865, EP-A-0 616 026, EP-A-0 616 028, DE-A-42 37 178 and U.S. Pat. No. 5,340,495 and in Schönfeldt (see above).

In general, the novel alkoxylate mixtures can be used in all areas where the action of surface-active substances is required.

The novel structures have lower aquatoxicity than known structures and are readily biodegradable, so that they are advantageously suitable for a multiplicity of applications.

The examples which follow illustrate the invention.

EXAMPLES

The 2-propylheptan-1-ol used was an isomer mixture comprising 87% of 2-propylheptan-1-ol, 11% of 2-propyl-4-methylhexan-1-ol and <1% of 2-propyl-5-methylhexan-1-ol.

Example 1

Alkoxylation of the 2-propylheptanol isomer Mixture with EO, PO and EO by Means of KOH Catalysis 1.1 2-Propylheptanol+5.2 EO+4.7 PO+2.3 EO 158.3 g (1.0 mol) of 2-propylheptanol isomer mixture and 3.8 g of 40% strength by weight potassium hydroxide solution were mixed and were dewatered in an autoclave at 80° C. and <10 mbar for 30 minutes. The autoclave was rendered inert with nitrogen and then heated to 145-155° C. First, 228.8 g (5.2 mol) of ethylene oxide were metered in to synthesize the first EO block and were allowed to react for about 1 hour until the pressure was constant. Thereafter, the internal temperature of the autoclave was reduced to 125-135° C., and 272.6 g (4.7 mol) of propylene oxide were then metered in to synthesize the PO block and were allowed to react for about 5 hours until the pressure was constant. Finally, the internal temperature was increased again to 145-155° C., and 101.2 g (2.3 mol) of ethylene oxide were metered in to synthesize the second EO block and were allowed to react for about 1 hour until the pressure was constant. Evacuation was effected for devolatilization, the reaction product was then brought to a pH of from 6 to 7 by adding acetic acid at 80° C. and finally the reactor was emptied.

The product had the following properties:

| | |
|---|---|
| Required OH number: 69.6 | Actual OH number: 71.0 |
| Wetting on textile surfaces (EN 1772): | 17 sec (23° C., 1 g/l in 2 g of sodium carbonate/l) |
| Foaming capacity (EN 122728): | about 15 ml (40° C.; 2 g/l; 1.8 mmol of $Ca^{2+}$ ions after 30 sec) |
| Surface tension (DIN 53914): | about 28.2 mN/m (1 g/l; 23° C.) |

1.2 2-Propylheptanol+0.7 EO+4.7 PO+2.3 EO

The preparation was carried out analogously to example 1.1. 158.3 g (1.0 mol) of 2-propylheptanol isomer mixture, 30.8 g (0.7 mol) of ethylene oxide for the first EO block, 272.6 g (4.7 mol) of propylene oxide for the PO block, 101.2 g (2.3 mol) of ethylene oxide for the second EO block and 2.8 g of 40% strength by weight potassium hydroxide solution were used.

The product had the following properties:

| | |
|---|---|
| Required OH number: 99.5 | Actual OH number: 97.0 |
| Wetting on textile surfaces (EN 1772): | 45 sec (23° C., 1 g/l in 2 g of sodium carbonate/l) |
| Foaming capacity (EN 122728): | about 10 ml (40° C.; 2 g/l; 1.8 mmol of $Ca^{2+}$ ions after 30 sec) |
| Surface tension (DIN 53914): | about 27.8 mN/m (1 g/l; 23° C.) |

1.3 2-Propylheptanol+3.2 EO+2.7 PO+2.3 EO

The preparation was carried out analogously to example 1.1. 158.3 g (1.0 mol) of 2-propylheptanol isomer mixture, 140.8 g (3.2 mol) of ethylene oxide for the first EO block, 156.6 g (2.7 mol) of propylene oxide for the PO block, 101.2 g (2.3 mol) of ethylene oxide for the second EO block and 2.78 g of 40% strength by weight potassium hydroxide solution were used.

The product had the following properties:

| | |
|---|---|
| Required OH number: 100.6 | Actual OH number: 101.0 |
| Wetting on textile surfaces (EN 1772): | 15 sec (23° C., 1 g/l in 2 g of sodium carbonate/l) |
| Foaming capacity (EN 122728): | about 15 ml (40° C.; 2 g/l; 1.8 mmol of $Ca^{2+}$ ions) |
| Surface tension (DIN 53914): | about 27.0 mN/m (1 g/l; 23° C.) |

1.4 2-Propylheptanol+2.7 EO+3.0 PO+2.3 EO

The preparation was carried out analogously to example 1.1. 158.3 g (1.0 mol) of 2-propylheptanol isomer mixture, 118.8 g (2.7 mol) of ethylene oxide for the first EO block, 174.0 g (3.0 mol) of propylene oxide for the PO block, 101.2 g (2.3 mol) of ethylene oxide for the second EO block and 2.76 g of 40% strength by weight potassium hydroxide solution were used.

The product had the following properties:

| | |
|---|---|
| Required OH number: 101.5 | Actual OH number: 102.4 |
| Wetting on textile surfaces (EN 1772): | 23 sec (23° C., 1 g/l in 2 g of sodium carbonate/l) |
| Foaming capacity (EN 122728): | about 10 ml (40° C.; 2 g/l; 1.8 mmol of $Ca^{2+}$ ions after 30 sec) |
| Surface tension (DIN 53914): | about 25.5 mN/m (1 g/l; 23° C.) |

1.5 2-Propylheptanol+2.7 EO+6.0 PO+2.3 EO

The preparation was carried out analogously to example 1.1. 158.3 g (1.0 mol) of 2-propylheptanol isomer mixture, 118.8 g (2.7 mol) of ethylene oxide for the first EO block, 348.0 g (6.0 mol) of propylene oxide for the PO block, 101.2 g (2.3 mol) of ethylene oxide for the second EO block and 3.63 g of 40% strength by weight potassium hydroxide solution were used.

The product had the following properties:

| | |
|---|---|
| Required OH number: 77.1 | Actual OH number: 81.5 |
| Wetting on textile surfaces (EN 1772): | 45 sec (23° C., 1 g/l in 2 g of sodium carbonate/l) |
| Foaming capacity (EN 122728): | <10 ml (40° C.; 2 g/l; 1.8 mmol of $Ca^{2+}$ ions after 30 sec) |
| Surface tension (DIN 53914): | about 28.3 mN/m (1 g/l; 23° C.) |

Example 2

Alkoxylation of the 2-propylheptanol isomer mixture with PO, EO, PO and EO by means of KOH catalysis

2.1 2-Propylheptanol+1.5 PO+2.7 EO+4.7 PO+2.3 EO 158.3 g (1.0 mol) of 2-propylheptanol isomer mixture and 3.7 g of 40% strength by weight potassium hydroxide solution were mixed and were dewatered in an autoclave at 80° C. and <10 mbar for 30 minutes. The autoclave was rendered inert with nitrogen and then heated to 125-130° C. First, 87.0 g (1.5 mol) of propylene oxide were metered in for synthesizing the first PO block and allowed to react for about 1.75 hours. The internal temperature of the autoclave was then increased to 145-155° C. and 118.8 g (2.7 mol) of ethylene oxide were metered in for synthesizing the first EO block and were allowed to react for 45 minutes until the pressure was constant. Thereafter, the internal temperature of the autoclave was reduced to 125-135° C., and 272.6 g (4.7 mol) of propylene oxide were then metered in for synthesizing the second EO block and were allowed to react for about 1.75 hours until the pressure was constant. Finally, the internal temperature was increased again to 145-155° C., and 101.2 g (2.3 mol) of ethylene oxide were metered in for synthesizing the second PO block and were allowed to react for about 1 hour until the pressure was constant. Evacuation was effected for devolatilization, the reaction product was then brought to a pH of from 6 to 7 by adding acetic acid at 80° C. and finally the reactor was emptied.

The product had the following properties:

| | |
|---|---|
| Required OH number: 75.9 | Actual OH number: 76.1 |
| Wetting on textile surfaces (EN 1772): | 39 sec (23° C., 1 g/l in 2 g of sodium carbonate/l) |
| Foaming capacity (EN 122728): | about 10 ml (40° C.; 2 g/l; 1.8 mmol of $Ca^{2+}$ ions after 30 sec) |
| Surface tension (DIN 53914): | about 28.1 mN/m (1 g/l; 23° C.) |

2.2 2-Propylheptanol+1.5 PO+1.7 EO+4.7 PO+2.3 EO 158.3 g (1.0 mol) of 2-propylheptanol isomer mixture and 3.47 g of 40% strength by weight potassium hydroxide solution were mixed and were dewatered in an autoclave at 80° C. and <10 mbar for 30 minutes. The autoclave was rendered inert with nitrogen and then heated to 125-130° C. First, 87.0 g (1.5 mol) of propylene oxide were metered in for synthesizing the first PO block and allowed to react for about 2 hours. The internal temperature of the autoclave was then increased to 145-155° C. and 74.8 g (1.7 mol) of ethylene oxide were metered in for synthesizing the first EO block and were allowed to react for 45 minutes until the pressure was constant. Thereafter, the internal temperature of the autoclave was reduced to 125-135° C., and 272.6 g (4.7 mol) of propylene oxide were then metered in for synthesizing the second PO block and were allowed to react for about 2 hours until the pressure was constant. Finally, the internal temperature was increased again to 145-155° C., and 101.2 g (2.3 mol) of ethylene oxide were metered in for synthesizing the second EO block and were allowed to react for about 1 hour until the pressure was constant. Evacuation was effected for devolatilization, the reaction product was then brought to a pH of from 6 to 7 by adding acetic acid at 80° C. and finally the reactor was emptied.

The product had the following properties:

| | |
|---|---|
| Required OH number: 80.7 | Actual OH number: 79.4 |
| Wetting on textile surfaces (EN 1772): | 61 sec (23° C., 1 g/l in 2 g of sodium carbonate/l) |
| Foaming capacity (EN 122728): | about 10 ml (40° C.; 2 g/l; 1.8 mmol of $Ca^{2+}$ ions after 30 sec) |
| Surface tension (DIN 53914): | about 28.2 mN/m (1 g/l; 23° C.) |

Further alkoxylates are summarized below in the table:

| EO (moleq.) | PO [moleq.] | EO [moleq.] | M (theor.) | Req. OHN | Act. OHN |
|---|---|---|---|---|---|
| 0.70 | 0.70 | 0.30 | 243.00 | 230.9 | 232.9 |
| 0.70 | 0.70 | 2.30 | 331.10 | 169.4 | 166.8 |
| 0.70 | 2.70 | 1.30 | 403.21 | 139.1 | 133.8 |
| 1.70 | 4.70 | 2.30 | 607.47 | 92.3 | 94.8 |
| 2.70 | 4.70 | 2.30 | 651.52 | 86.1 | 86.0 |
| 3.20 | 0.70 | 1.30 | 397.17 | 141.2 | 136.9 |
| 3.20 | 2.70 | 0.30 | 469.28 | 119.5 | 116.1 |
| 3.20 | 2.70 | 1.30 | 513.33 | 109.3 | 109.4 |
| 3.20 | 4.70 | 1.30 | 629.49 | 89.1 | 90.3 |
| 3.70 | 4.70 | 2.30 | 695.57 | 80.6 | 80.4 |
| 4.70 | 4.70 | 2.30 | 739.62 | 75.8 | 74.8 |
| 5.70 | 0.70 | 0.30 | 463.25 | 121.1 | 120.4 |
| 5.70 | 0.70 | 2.30 | 551.35 | 101.7 | 104.9 |
| 5.70 | 2.70 | 1.30 | 623.46 | 90.0 | 88.6 |
| 5.70 | 4.70 | 0.30 | 695.57 | 80.6 | 75.9 |
| 5.70 | 4.70 | 2.30 | 783.67 | 71.6 | 72.9 |

The invention claimed is:

1. An alkoxylate mixture comprising alkoxylates of the formula (I)

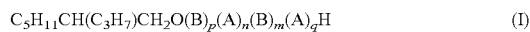

$$C_5H_{11}CH(C_3H_7)CH_2O(B)_p(A)_n(B)_m(A)_qH \quad (I)$$

where
A is ethyleneoxy,
B propyleneoxy
groups A and B being present in the form of blocks in the stated sequence,
p is a number from 1 to 3,
n is a number from 0.25 to 10,
m is a number from 2 to 10,
q is a number from 1 to 5,
from 85 to 96% by weight of alkoxylates A1, in which $C_5H_{11}$ is n-$C_5H_{11}$, and
from 4 to 15% by weight of alkoxylates A2, in which $C_5H_{11}$ is $C_2H_5CH(CH_3)CH_2$ and/or $CH_3CH(CH_3)CH_2CH_2$, being present in the mixture.

2. The alkoxylate mixture according to claim 1, wherein $C_3H_7$ is n-$C_3H_7$.

3. A process for the preparation of an alkoxylate mixture according to claim 1 comprising reacting a 2-propyl heptanol mixture with ethylene oxide and propylene oxide under alkoxylation conditions.

4. The process for the preparation of an alkoxylate mixture according to claim 3, wherein the reacting a 2-propyl heptanol mixture with ethylene oxide and propylene oxide comprises a double metal cyanide compound as a catalyst.

5. An emulsifier, foam regulator and wetting agent for hard surfaces comprising the alkoxylate mixture according to claim 1.

6. A method for preparing detergents, surfactant formulations for cleaning hard surfaces, humectants, cosmetic, pharmaceutical and crop protection formulations, finishes, coating materials, adhesives and leather degreasing agents, formulations for the textile industry comprising adding the alkoxylate mixture according to claim 1.

7. A detergent, cleaning agent, wetting agent, coating material, adhesive, leather degreasing agent, humectant or textile treatment composition, additive for mineral building materials or cosmetic, pharmaceutical or crop protection formulation comprising an alkoxylate mixture according to claim 1.

8. A processing method comprising one selected from the group consisting of emulsifying, foam regulating and wetting of hard surfaces employing the alkoxylate mixture according to claim 1, wherein the processing method is one selected from the group consisting of fiber processing, metal processing, food processing, water treatment, paper processing, mineral processing, fermentation, emulsion polymerization and preparing mineral building materials.

* * * * *